United States Patent
Huang et al.

(10) Patent No.: US 12,344,835 B2
(45) Date of Patent: Jul. 1, 2025

(54) ***PENICILLIUM OXALICUM* SDF-25 STRAIN AND APPLICATION THEREOF**

(71) Applicant: HEBEI UNIVERSITY OF SCIENCE AND TECHNOLOGY, Hebei (CN)

(72) Inventors: Yali Huang, Hebei (CN); Huizhen Xing, Hebei (CN); Yuanyuan Huang, Hebei (CN); Li Zhang, Hebei (CN); Zaixing Li, Hebei (CN)

(73) Assignee: HEBEI UNIVERSITY OF SCIENCE AND TECHNOLOGY, Shijiazhuang (CN)

( * ) Notice: Subject to any disclaimer, the term of this patent is extended or adjusted under 35 U.S.C. 154(b) by 868 days.

(21) Appl. No.: 17/502,259

(22) Filed: Oct. 15, 2021

(65) Prior Publication Data
US 2022/0033762 A1 Feb. 3, 2022

Related U.S. Application Data

(63) Continuation of application No. PCT/CN2020/133526, filed on Dec. 3, 2020.

(30) Foreign Application Priority Data

Apr. 3, 2020 (CN) .......................... 202010258362.6

(51) Int. Cl.
*C12N 1/14* (2006.01)
*C05F 17/20* (2020.01)
*C12R 1/80* (2006.01)

(52) U.S. Cl.
CPC .............. *C12N 1/145* (2021.05); *C05F 17/20* (2020.01); *C12R 2001/80* (2021.05)

(58) Field of Classification Search
CPC ............ C12N 1/145; C05F 17/20; C12R 1/80
See application file for complete search history.

(56) References Cited

FOREIGN PATENT DOCUMENTS

| CN | 103740597 A | 4/2014 |
|---|---|---|
| CN | 105296363 A | 2/2016 |
| CN | 111534439 A | 8/2020 |

OTHER PUBLICATIONS

Xing, Huizhen et al., Screening, Identification and Characterization of A Low-temperature Maize Straw Degradation Fungus, Microbiology China, vol. 47, No. 9, Sep. 20, 2020 (Sep. 20, 2020), pp. 2923-2933.
Mu, Chunlei et al., Screening and Identification of A Cold-adapted Cellulase-producing Strains and Characterization of Cellulase: Microbiology China, vol. 40, No. 7, 2013, pp. 1193-1201.
Li et al., Optimizing Production of Pectinase from Orange Peel by Penicillium oxalicum PJ02 Using Response Surface Methodology, Waste Biomass Valor, vol. 6, 2014, pp. 13-22.
Dhakar et al., Cold, pH and salt tolerant Penicillium spp. inhabit the high altitude soils in Himalaya, India, World J Microbiol Biotechnol, vol. 30, 2013, pp. 1315-1324.
International Search Report of PCT/CN2020/133526, mailed on Mar. 5, 2021.

*Primary Examiner* — Robert A Zeman
(74) *Attorney, Agent, or Firm* — Leason Ellis LLP

(57) ABSTRACT

Disclosed are a *Penicillium oxalicum* SDF-25 strain and applications thereof, which relate to the technical field of environmental microorganisms. The *Penicillium oxalicum* SDF-25 strain has a strain preservation number of CGMCC No. 19272. The *Penicillium oxalicum* SDF-25 strain can be applied to straw degradation. The *Penicillium oxalicum* SDF-25 strain provided in the present solution can grow normally at 6 to 37° C. The *Penicillium oxalicum* SDF-25 strain can secrete a large amount of carboxymethyl cellulase at 10 to 16° C., and still produce enzyme at 6° C. The highest enzymatic activity can reach 993.3 U/mL.

5 Claims, 6 Drawing Sheets
Specification includes a Sequence Listing.

PENICILLIUM OXALICUM SDF-25 STRAIN AND APPLICATION THEREOF

CROSS-REFERENCE TO RELATED APPLICATIONS

This application is a continuation application of International Application No. PCT/CN2020/133526, filed on Dec. 3, 2020, which claims priority to Chinese Patent Application No. CN 202010258362.6, filed on Apr. 3, 2020. The disclosures of the aforementioned applications are hereby incorporated herein by reference in their entireties.

TECHNICAL FIELD

The present application relates to the *Penicillium oxalicum* SDF-25 strain and applications thereof, and belongs to the field of environmental microorganisms.

BACKGROUND

Crop straw is an important biomass resource because of its huge annual output. The effective use of straw directly affects the sustainable development of modern agriculture. Straw returning is an effective approach of the straw utilization. Straw returning plays an important role in reducing soil water potential, increasing soil temperature and hydrolase activity, increasing soil organic matter content, and enhancing microbial functional diversity of soil. However, in some areas where wheat is planted after corn, due to insufficient light and heat resources, the corn-wheat planting interval is short and the temperature in wheat planting season is low, which can result in the corn straw not being rapidly degraded after being returned to the field. If the corn straw cannot be rapidly degraded, it will lead to difficulty of emergence and rooting of late-planted wheat, and decrease in the overwintering ability of the late-planted wheat. The above-mentioned corn-wheat planting interval refers to a period of time during which wheat can be planted after corn.

A straw-degrading microorganism is an indispensable driving force for straw degradation. However, due to the small number of straw-degrading microorganisms in the original soil ecological environment, the degradation efficiency of the straw is low and degradation time is long. In the case of short crop planting interval, natural degradation of straw cannot meet needs of crop planting. Therefore, in order to accelerate decomposition of straw in soil, it is necessary to use efficient straw-degrading bacteria. Since the isolation of cellulose-degrading bacteria from soil in 1912, researchers have conducted a lot of screening and applications of cellulose-degrading bacteria. Some researchers obtained filamentous fungi that can degrade rice straw cellulose at 28 to 37° C. by performing enrichment culture on samples. Some researchers isolated mold F6 from soil which could degrade 44.8% corn straw after being cultured at 28° C. for 15 days (d). Some studies have shown that *Trichoderma reesei* RUT-C30 is capable of producing a filter paper enzyme (FPase) with an activity of 5.02 U/mL and a carboxymethyl cellulase (CMCase) with an activity of 4.2 U/mL. However, existing studies on cellulose-degrading bacteria mainly focus on normal temperature and high temperature environments, and studies on cellulose-degrading bacteria in low temperature environment are relatively scarce. Especially when the soil temperature is below 16° C., the existing microorganisms have poor straw degradation ability.

In a temperate monsoon climate region, a planting interval for wheat is less than one month, and the average soil temperature at a depth of 0 to 20 cm is 6 to 18° C. when wheat is planted. The development and application of low-temperature straw-degrading microbial inoculum suitable for the soil temperature is of great significance for promoting corn straw to return to field quickly and for improving soil fertility and effective use of biomass resources.

SUMMARY

Technical Problems

To solve the problems of low straw degradation efficiency, slow propagation rate, and low cellulase yield and activity of existing straw-degrading microorganisms in a low temperature environment, the present application provides *Penicillium oxalicum* SDF-25 and applications thereof, so as to improve the straw degradation efficiency by microorganisms in a low temperature environment.

Technical Solutions

In a first aspect, the present application provides the *Penicillium oxalicum* SDF-25 strain, with a preservation number of CGMCC No. 19272. A fungus was isolated from soil. After being identified, we named the isolated fungus as *Penicillium oxalicum* SDF-25, and preserved in China General Microbiological Culture Collection Center, referred to as CGMCC on Jan. 16, 2020, with a preservation number of CGMCC NO. 19272, and the preservation address is Institute of Microbiology, Chinese Academy of Sciences, No. 3, Courtyard 1, Beichen West Road, Chaoyang District, Beijing.

In a second aspect, the present application provides applications of *Penicillium oxalicum* SDF-25 in straw degradation.

In a third aspect, the present application provides an inoculant prepared from *Penicillium oxalicum* SDF-25, which includes a thallus adsorption substrate and *Penicillium oxalicum* SDF-25. *Penicillium oxalicum* SDF-25 may be combined with the adsorption substrate in the form of bacterial powder to prepare the inoculant.

As an embodiment of the present application, the thallus adsorption substrate is light calcium carbonate.

The light calcium carbonate serving as the thallus adsorption substrate may enable a cryopreservation time of viable *Penicillium oxalicum* SDF-25 to be more than one year.

As an embodiment of the present application, the number of the viable *Penicillium oxalicum* SDF-25 strains in the inoculant is $\geq 2 \times 10^8$ cfu/g.

In a fourth aspect, the present application provides a preparation method of an inoculant, which includes the following steps:

step a: activating *Penicillium oxalicum* SDF-25 to obtain strains;

step b: performing liquid culture on the strains to obtain a culture broth containing *Penicillium oxalicum* SDF-25;

step c: fermenting the culture broth to obtain a fermentation broth containing *Penicillium oxalicum* SDF-25;

step d: performing amplification culture on the fermentation broth to obtain a seed broth containing *Penicillium oxalicum* SDF-25; and step e: centrifuging the seed broth, removing a supernatant, finally adding the adsorption substrate and drying to obtain the inoculant containing *Penicillium oxalicum* SDF-25.

As an embodiment of the present application, in step a, activating *Penicillium oxalicum* SDF-25 includes: streaking cryopreserved *Penicillium oxalicum* SDF-25 onto a plate medium made of a PDA medium, and culturing at a temperature of 10 to 20° C. for 12 to 24 hours (h).

As an embodiment of the present application, in step b, performing liquid culture on the strains includes: obtaining hyphae of the *Penicillium oxalicum* SDF-25 from the strains obtained in step a, inoculating into a conical flask containing a PD medium (liquid), and performing shaking culture at 150 to 250 r/min and 10 to 20° C. for 24 to 48 h.

As an embodiment of the present application, in step c, fermenting the culture broth includes: inoculating the culture broth obtained in step b into a liquid enzyme production medium, and performing fermentation culture at 10 to 20° C. and 150 to 250 r/min for 2 to 3 days (d), an inoculation volume of the culture broth being 5% to 10% of a volume of the liquid enzyme production medium.

As an embodiment of the present application, in step d, performing amplification culture on the fermentation broth includes: inoculating the fermentation broth obtained in step c into a seeding tank containing a PD medium (liquid), and fermenting at 10 to 20° C. and 150 to 200 r/min for 24 to 48 h, an inoculation volume of the fermentation broth being 2% to 5% of a volume of the PD medium (liquid).

Advantageous Effects of the Disclosure

Compared with the prior art, the present solution has the following advantages.

The *Penicillium oxalicum* SDF-25 strain provided in the present application can normally grow at 6 to 37° C., and the enzymatic activity of carboxymethyl cellulase produced by *Penicillium oxalicum* SDF-25 is very high in a temperature range from 10 to 16° C. *Penicillium oxalicum* SDF-25 may be inoculated into the liquid enzyme production medium with a pH value of 5 to 10 in an inoculation amount of 2%, and cultured at a temperature of 10 to 16° C., and the highest activity of the enzyme produced by *Penicillium oxalicum* SDF-25 can reach 993.3 U/mL. Furthermore, *Penicillium oxalicum* SDF-25 can still grow and produce enzymes at a low temperature of 6° C.

*Penicillium oxalicum* SDF-25 provided by the present application may be inoculated into a straw degradation medium in an inoculation amount of 2%, cultured at a temperature of 16° C. for 15 d, and detected. The degradation rate of *Penicillium oxalicum* SDF-25 on corn straw may be as high as 48.6%. When the temperature is changed from 16° C. to 10° C., with the other conditions remaining unchanged, the degradation rate of the *Penicillium oxalicum* SDF-25 strain on corn straw can still reach 40%. It indicates that the *Penicillium oxalicum* SDF-25 strain provided by the present application has the ability of normal growth and synthesis of high-activity cellulase under low temperature conditions, and has great potential to promote rapid straw returning in autumn and winter when the temperature is low.

The inoculant prepared by the method for preparing an inoculant from *Penicillium oxalicum* SDF-25 provided in the present application can be adapted to a low temperature environment and can grow rapidly in straw, effectively improve the straw degradation rate, and shorten the straw degradation time. In step e, the adsorption substrate is added and dried, and a method of using a substrate to adsorb spores of strains can ensure the activity of thallus in the inoculant.

DETAILED DESCRIPTION OF ILLUSTRATIVE EMBODIMENTS

Embodiment 1

Screening process of *Penicillium oxalicum* SDF-25

1.1 Samples and Media

1.1.1 Samples

Figure 1:
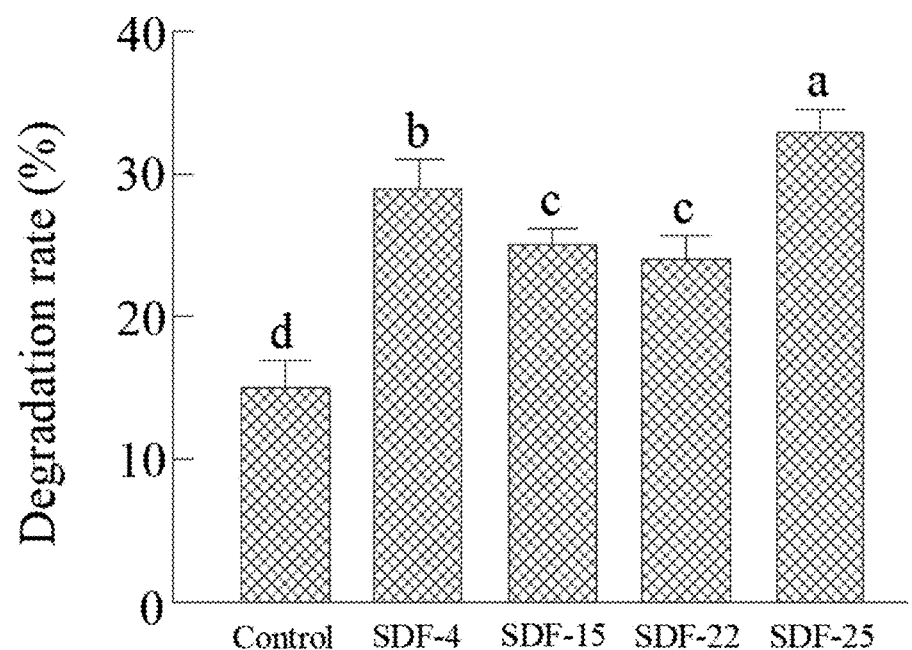
FIG. 1 is a column diagram of the degradation rates of four secondary screened strains in corn straw in Embodiment 1 of the present application.

Samples were collected from soils in cold climate regions of China such as Inner Mongolia Autonomous Region, Heilongjiang Province, and Bashang Region of Hebei Province. When the samples were collected, impurities such as animal and plant residues on the soil surface were removed to obtain soil samples. The soil samples were placed in sterilization pouches that had been sterilized, and the sterilization pouches were placed in ice boxes and transported back to a laboratory. After being transported back to the laboratory, the soil samples were stored in a refrigerator at 4° C.

1.1.2 Media

PD medium: the PD medium is a common medium in the art. The PD medium is a mixture containing potato, glucose, and water. The PD medium of the present embodiment had a volume of 1,000 mL and contained 200 g of potato and 20 g of glucose.

PDA medium: 3 mL of gentamicin sulfate injection and 15 to 20 g of agar were added into the above-mentioned PD medium to obtain the PDA medium.

Cellulose-congo red medium: 5 g of sodium carboxymethyl cellulose (CMC-Na), 2 g of $(NH_4)_2SO_4$, 1 g of $KH_2PO_4$, 0.5 g of $MgSO_4 \cdot 7H_2O$, 0.5 g of NaCl, 1 g of $NaNO_3$, 0.5 g of peptone, 0.5 g of yeast powder, 0.2 g of congo red, and 20 g of agar were mixed to a volume of 1,000 mL, and the pH value was 7.0.

Liquid enzyme production medium: 200 g of potato, 20 g of glucose, and 10 g of CMC-Na were mixed to a volume of 1,000 mL.

Corn straw medium: 2 g of corn straw (crushed, passed through a 40-mesh sieve and dried at 50° C. to a constant weight), and 30 mL of nutrient solution were mixed. The nutrient solution contained 3.0 g of urea, 6.0 g of $(NH_4)_2SO_4$, 3.0 g of peptone, 0.1 g of $CaCl_2$, 0.5 g of $MgSO_4 \cdot 7H_2O$, 1.0 g of $K_2HPO_4$, 0.1 g of NaCl, 0.05 g of $FeSO_4 \cdot 7H_2O$, 0.016 g of $MnSO_4 \cdot 7H_2O$, 0.014 g of $ZnSO_4 \cdot 7H_2O$, 0.037 g of $COCl_2 \cdot 6H_2O$, and 1,000 mL of distilled water.

1.2 Isolation and Purification 5 g of soil sample was weighed and placed into 45 mL of sterile water to form a mixture I. The mixture I was shaken at 200 r/min for 30 minutes (min) on a shaker to be mixed well; then, the mixture I was progressively diluted to $10^{-2}$, $10^{-3}$ and $10^{-4}$ times with sterile normal saline. 100 μL of liquid at dilutions of $10^{-2}$, $10^{-3}$ and $10^{-4}$ was respectively pipetted onto a plate medium I made of the above-mentioned PDA medium. The liquid at each dilution was pipetted for 3 times onto 3 plate media I, and the liquid at 3 dilutions were completely pipetted onto 9 plate media I. After all the plate media I were placed and cultured in a constant temperature incubator at 16° C. for 3 days (d), colonies I grew on the plate culture media I. Colonies I of different morphologies were picked up from all of the colonies I, and each picked colony I was streaked 3 times for purification to obtain multiple colonies II. Then 40 colonies II to be cultured were selected from the multiple colonies II, and were respectively inoculated on a test tube slant medium made of 40 PDA media. All of the colonies II inoculated on the test tube slant medium were cultured at 16° C. until the slant was full, and a total of 40 strains to be screened were obtained. The 40 strains to be screened were numbered from SDF-1 to SDF-40 sequentially and were stored at 4° C. for future use.

1.3 Screening of Low Temperature Cellulose-Degrading Strains

1.3.1 Primary Screening

The strains to be screened that were stored at a low temperature were inoculated onto a plate medium II (made of the above-mentioned PDA medium) and activated to form a colony III. A punch with a diameter of 5 mm was used to collect bacterial clumps I from an eugonic edge region of the colony III. The bacterial clumps I were inoculated onto the cellulose-congo red medium, and cultured at a constant temperature of 16° C. for 3 d to form a colony IV. When a hydrolytic circle near the colony IV was observed, the diameter (d) of the colony IV and the diameter (D) of the hydrolytic circle were measured and recorded, and a value of D/d was calculated. 3 bacterial clumps I were correspondingly obtained from each strain to be screened, and 3 groups of diameter values were obtained. A mean value of the 3 groups of diameter values was taken as corresponding d value and D value of each strain to be screened.

After the preliminary screening on the cellulose-congo red medium, among the 40 strains that were screened, 21 strains had cellulose degradation capacity, and a ratio (D/d) of the diameter of the hydrolytic circle to the diameter of the colony of 13 screened strains was greater than 2.0, as shown in Table 1 (the 13 screened strains with a D/d ratio greater than 2.0 were named primary screened strains).

TABLE 1

Sizes of hydrolytic circles of 13 primary screened strains on the cellulose-congo red medium

| Strain No. | D (mm) | d (mm) | D/d |
|---|---|---|---|
| SDF-2 | 21.5 ± 0.71 | 9.0 ± 0.00 | 2.388 ± 0.07 |
| SDF-3 | 21.5 ± 3.54 | 10.0 ± 1.41 | 2.146 ± 0.05 |
| SDF-4 | 41.5 ± 10.61 | 17.0 ± 4.24 | 2.439 ± 0.01 |
| SDF-9 | 15.2 ± 0.35 | 7.2 ± 0.35 | 2.105 ± 0.05 |
| SDF-13 | 21.5 ± 0.71 | 10.0 ± 1.41 | 2.166 ± 0.23 |
| SDF-15 | 27.0 ± 4.24 | 11.5 ± 2.12 | 2.354 ± 0.06 |
| SDF-17 | 23.0 ± 1.41 | 10.5 ± 0.70 | 2.191 ± 0.01 |
| SDF-18 | 30.6 ± 5.46 | 12.8 ± 1.92 | 2.391 ± 0.22 |
| SDF-21 | 24.3 ± 0.58 | 9.6 ± 0.57 | 2.522 ± 0.13 |
| SDF-22 | 25.5 ± 0.71 | 12.2 ± 0.35 | 2.081 ± 0.01 |
| SDF-25 | 25.5 ± 0.71 | 11.7 ± 0.35 | 2.170 ± 0.00 |
| SDF-30 | 29.5 ± 2.12 | 13.0 ± 1.41 | 2.273 ± 0.08 |
| SDF-31 | 39.0 ± 1.41 | 17.2 ± 1.06 | 2.262 ± 0.05 |

In Table 1, "D" refers to diameter of hydrolytic circle; "d" refers to diameter of colony.

1.3.2 Secondary Screening

The obtained 13 primary screened strains were activated on a plate medium III (made of the above-mentioned PDA medium) to form colonies V. An inoculating loop was used to pick fresh hyphae I from the colonies V and placed them in a PD medium, and the fresh hyphae I were cultured at 16° C. and 200 r/min for 48 hours (h) to form strains I. The strains I were inoculated into 50 mL of liquid enzyme production medium according to an inoculation volume of 2%, and were subjected to liquid fermentation culture under constant temperature shaking (16° C. and 200 r/min). After 3 days, 10 mL of sample was taken and put into a centrifuge tube to obtain a mixture II. The mixture II was centrifuged at 10,000 r/min for 10 min, and the supernatant was a crude enzyme solution. The crude enzyme solution contained carboxymethyl cellulase (CMCase) produced by the primary screened strains. An activity of CMCase produced by the primary screened strains was determined by using a 3,5-dinitrosalicylic acid (DNS) method as follows. A measurement group was set, and a glucose amount m1 was obtained by the following steps: step 1:1.0 mL of the above-mentioned crude enzyme solution was taken and added into 4.0 mL of sodium carboxymethyl cellulose buffer solution (CMC buffer solution) to obtain a mixture III; step 2: the mixture III reacted in a water bath at 50° C. for 20 min and then was taken out to obtain a mixture IV; step 3: 3.0 mL of 3,5-dinitrosalicylic acid developing solution (DNS developing solution) was added into the mixture IV, color was developed in a boiling water bath for 10 min, and then the mixture IV was cooled to obtain a mixture V having a color; and step 4: an optical density value (OD value) of the mixture V was measured by using a UV spectrophotometer; a wavelength of the UV spectrophotometer was set to 490 nm and the OD value of the mixture V was measured; the measured OD value was compared with a standard glucose curve to obtain the glucose amount (m1). A control group was set as follows and the glucose amount m2 was obtained:

no CMC buffer solution was added into the crude enzyme solution in the control group. Namely, the crude enzyme solution in the control group was treated from the above-mentioned step 2 on, with the treatment conditions being consistent with those in the measurement group, and finally the glucose amount m2 was measured. The corresponding enzymatic activity (unit: U/mL) of the primary screened strains was calculated by the following formula: U=(m1−m2)/20×dilution fold. The corresponding enzymatic activity of the primary screened strains could indicate a transfer ability of the CMCase produced by the primary screened strains to CMC buffer solution (substrate).

Secondary screening results are shown in Table 2, and the corresponding enzymatic activities of the 13 primary screened strains were between 233.3 U/mL and 703.3 U/mL. The SDF-25 strain had the highest corresponding enzymatic activity, followed by SDF-4, SDF-15 and SDF-22, with the corresponding enzymatic activities of the 4 strains being 600.3 U/mL, 565.3 U/mL, 636.3 U/mL, and 703.3 U/mL, respectively, which were significantly higher than those of the other 9 primary screened strains. The 4 primary screened strains with higher corresponding enzymatic activities were named secondary screened strains.

TABLE 2

Corresponding enzyme activities of 13 primary screened strains

| Strain No. | Corresponding enzymatic activity (U/mL) |
|---|---|
| SDF-2 | 362.7 ± 0.35 i |
| SDF-3 | 416.7 ± 0.70 f |
| SDF-4 | 600.3 ± 0.37 c |
| SDF-9 | 388.3 ± 0.12 g |
| SDF-13 | 285.0 ± 0.32 k |
| SDF-15 | 565.3 ± 0.18 d |
| SDF-17 | 313.3 ± 0.62 j |
| SDF-18 | 383.3 ± 0.16 h |
| SDF-21 | 233.3 ± 0.54 m |
| SDF-22 | 636.3 ± 0.67 b |
| SDF-25 | 703.3 ± 0.23 a |
| SDF-30 | 281.7 ± 0.19 l |
| SDF-31 | 486.7 ± 0.21 e |

1.4 Growth of Secondary Screened Strains at Different Temperatures

Four bacterial clumps, namely, SDF-25 bacterial clump, SDF-4 bacterial clump, SDF-15 bacterial clump, and SDF-22 bacterial clump, were obtained from the obtained 4 secondary screened strains. The above-mentioned four bacterial clumps were inoculated onto PDA media respectively. The number of each bacterial clump was 5, and the 5 bacterial clumps were respectively placed in constant temperature incubators at 6° C., 10° C., 16° C., 28° C. and 37° C. for static culture for 7 d, so as to obtain 20 colonies VI.

The growth rate of each colony VI at different temperatures was determined and recorded. The growth rate of the 20 colonies VI could reflect the growth rate of the 4 secondary screened strains at different temperatures. The growth rates of the 4 secondary screened strains at 6° C., 10° C., 16° C., 28° C., and 37° C. were compared by a strain growth rate determination method. It can be seen from Table 3 that among the 4 secondary screened strains, the growth rate of the SDF-25 strain was the highest at the temperature of 16° C.; and the SDF-25 strain can grow normally in the temperature range of 6 to 37° C., and has low-temperature adaptability, so it has the potential to promote rapid straw returning in autumn and winter.

TABLE 3

Low-temperature growth rate millimeter per day (mm/d) of 4 secondary screened strains

| Strain No. | 6□ | 10□ | 16□ | 28□ | 37□ |
|---|---|---|---|---|---|
| SDF-4 | 0.714 | 1.171 | 3.224 | 3.128 | 3.083 |
| SDF-15 | 0.714 | 1.114 | 3.112 | 3.015 | 3.117 |
| SDF-22 | 0.714 | 1.785 | 3.267 | 3.243 | 3.216 |
| SDF-25 | 1.071 | 2.314 | 3.392 | 3.341 | 3.329 |

1.5 Determination of Straw Degradation Rate of Strains

The obtained 4 secondary screened strains were activated on plate media IV (made of the above-mentioned PDA medium) to form colonies VI, An inoculating loop was used to pick fresh hyphae II from the colonies VI and placed them in PD media, and the fresh hyphae II were cultured at 16° C. and 200 r/min for 48 h to form strains II. The strains II were inoculated into corn straw media (a control group was set, where an equivalent amount of sterile water was added into a corn straw medium in the control group) according to an inoculation volume of 2%, and were cultured at a constant temperature of 16° C. After 15 d, straw materials were collected through filtration using a filter paper. The straw materials were washed repeatedly with distilled water for 3 times, and then dried at 80° C. to a constant weight. A weight loss rate was calculated. Each secondary screened strain was correspondingly inoculated on 3 corn straw media. 3 weight loss rates were obtained, and a mean value of the 3 weight loss rates was taken as a corresponding weight loss rate of each secondary screened strain.

The results are shown in FIG. 1. At 15 d, the straw degradation rates of the 4 secondary screened strains, SDF-4, SDF-15, SDF-22, and SDF-25, were 29.4%, 25.7%, 24.6% and 33.6%, respectively. The straw degradation rates of the 4 secondary screened strains were significantly higher than that of the control group. Compared with the control group, the straw degradation rates of the 4 secondary screened strains were greater by 93.4%, 69.1%, 61.8% and 121%, respectively. The results indicated that the 4 secondary screened strains can effectively promote the degradation of corn straw at low temperature, and have good practical applications. Among the 4 secondary screened strains, the enzymatic activity of cellulase produced by the SDF-25 strain and the corn straw degradation rate of the SDF-25 strain were significantly higher than those of the other 3 secondary screened strains. It is to be noted that in FIGS. 1, and 6 to 11, small letters above each columnar unit indicate that there is a significant difference at the 0.05 level between different processing.

1.6 Strain Identification

1.6.1 Morphological Observation

Bacterial clumps of the SDF-25 strains with a diameter of 5 mm were inoculated on a PDA medium and cultured at 16° C., and growth and morphological characteristics of the colonies were observed. The morphology of conidiophore of the strain was observed by a coverslip inserting culture method. An appropriate amount of cultured hyphae was taken on a glass slide by using a sterile forceps. The hyphae were stirred to spread uniformly. The glass slide was covered with a coverslip, and placed under a microscope, and microscopic characteristics of conidia were observed.

Figure 2:
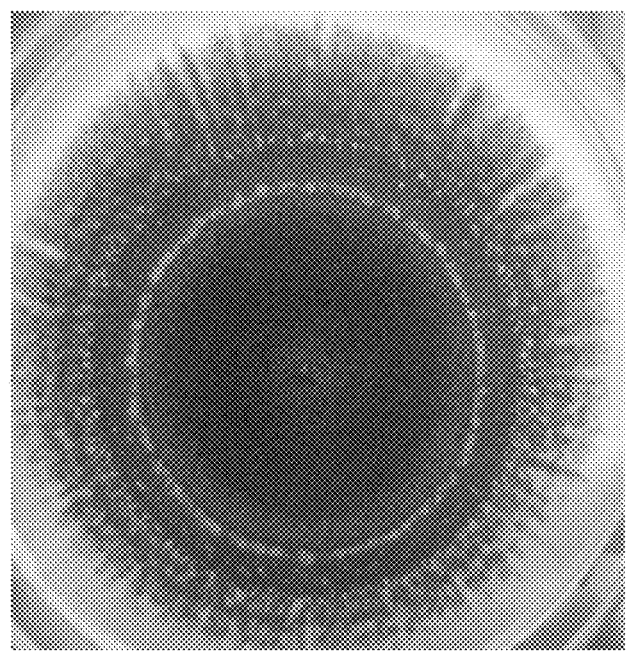
FIG. 2 is a diagram of colony morphology of *Penicillium oxalicum* SDF-25 on a PDA medium in Embodiment 1 of the present application.
Figure 3:
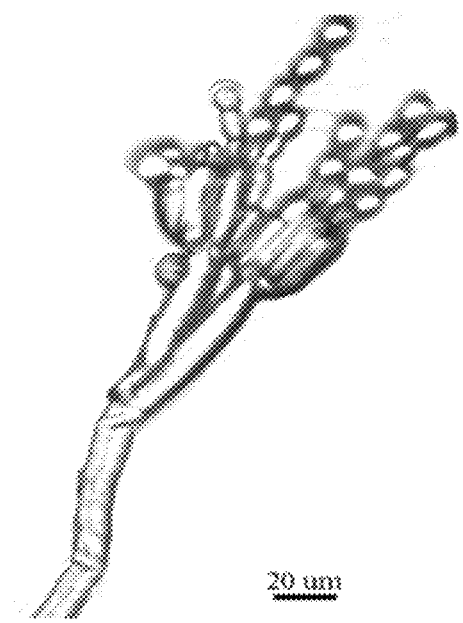
FIG. 3 is a morphology diagram of a conidiophore of *Penicillium oxalicum* SDF-25 in Embodiment 1 of the present application.
Figure 4:
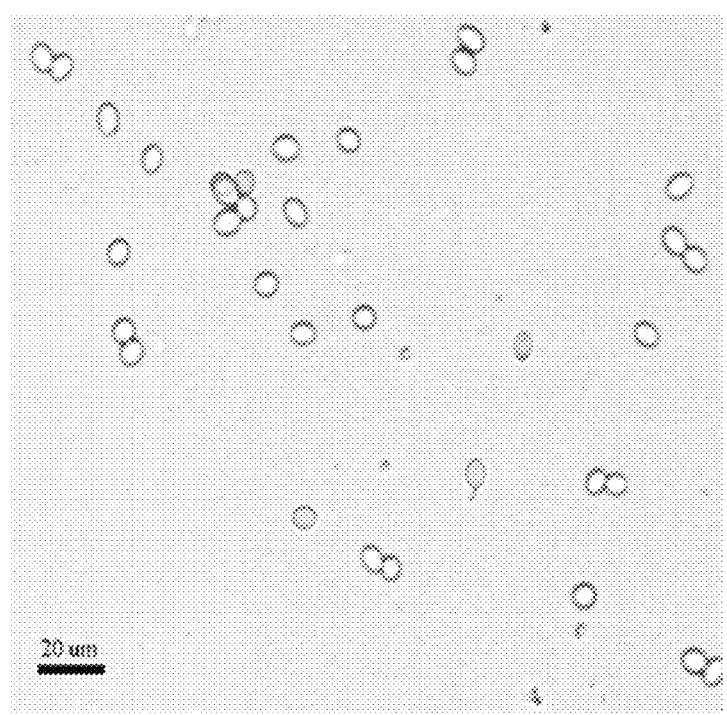
FIG. 4 is a morphology diagram of a conidium of *Penicillium oxalicum* SDF-25 in Embodiment 1 of the present application.

The SDF-25 strains were cultured on a PDA medium at 16° C. Firstly, white and subround colonies appeared. After 5 days, the colonies became dark green, and had dense hyphae, concentric rings and smooth edges; the colony surface was powdery, and hyphal villi had transparent secretion, as shown in FIG. 2. The conidiophore of the strain was observed under the microscope, and had multiple branches in a dispersed or serial spore chain, as shown in FIG. 3. After the spore chain matured, it fell off to form a single spore, and the conidia were subround and smooth, with the sizes being 2.2 to 3.0 μm, as shown in FIG. 4. Based on the colony morphology and conidium structure characteristics, the SDF-25 strains were preliminarily identified as *Penicillium* by comparison and analysis according to "Fungus Identification Manual" and "Chinese Flora Fungorum Sinicorum".

1.6.2 Molecular Biological Identification

DNA of the SDF-25 strain was extracted by using a fungal genomic DNA extraction kit (Beijing Solarbio Science & Technology Co., Ltd.). An rDNA sequence of an ITS region of the strain was amplified by using the fungal universal primers ITS4 (5'-TCCTCCGCTTATTGATATGC-3') and ITS6 (5'-GAAGGTGAAGTCGTAACAAGG-3'). The PCR reaction system (25 μL) included: 2 μL of 10× buffer, 2 μL of DNA template, 2 μL of dNTP, 1 μL of each primer, 0.2 μL of r-Tap enzyme, and 11.8 μL of ddH$_2$O. The PCR reaction conditions were: 94° C. for 5 min; 94° C. for 1 min, 53° C. for 1 min, 72° C. for 1 min, 33 cycles; and 72° C. for 10 min.

Amplified products were sequenced by Sangon Biotech (Shanghai) Co., Ltd. Sequencing results were subjected to BLAST (Basic Local Alignment Search Tool) comparison in the database of American National Center for Biotechnology (NCBI). Finally, a phylogenetic tree was constructed by a Neighbor-Joining method of MEGA 5.1 to determine the phylogenetic position of the SDF-25 strain.

Figure 5:
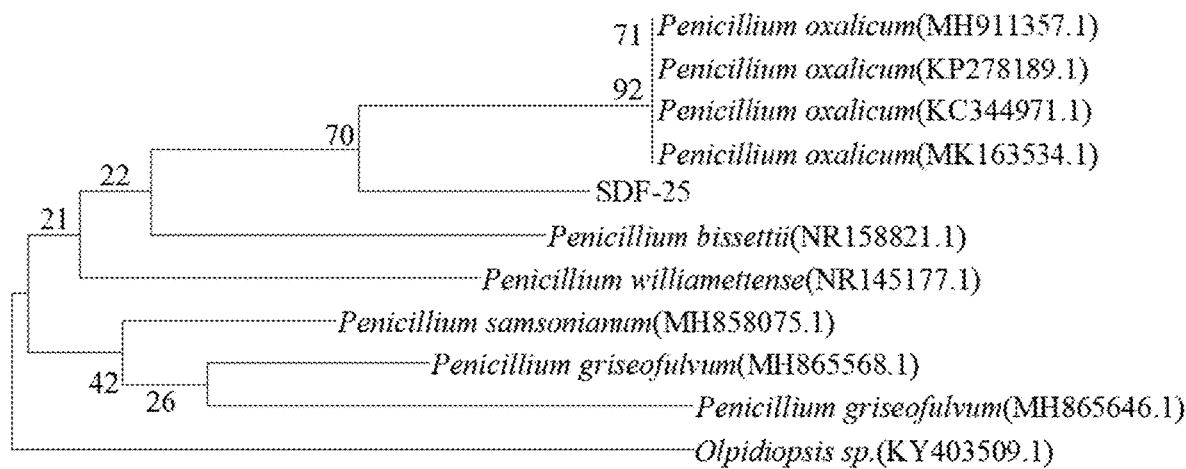
FIG. 5 is a phylogenetic tree of *Penicillium oxalicum* SDF-25 constructed based on an ITS gene sequence similarity in Embodiment 1 of the present application.

PCR amplification of the ITS sequence was performed by using the DNA of the SDF-25 strain as a template, and an rDNA fragment of ITS obtained by sequencing had a length of 616 bp (SEQ ID NO: 3). The sequencing results were subjected to BLAST comparison in the database of NCBI, and the phylogenetic tree was constructed by the Neighbor-Joining method of MEGA 5.1, as shown in FIG. 5. Through the phylogenetic tree, the SDF-25 strain was found to be in the same branch as strains such as *P. oxalicum*_strain (accession number: MH911357.1) and *P. oxalicum*_strain (accession number: MK 163534.1). Based on comprehensive analysis of colony characteristics and phylogeny, the SDF-25 strain was identified as *Penicillium oxalicum* (*P. oxalicum*), and its accession number was MN 841785 after 16S rDNA sequence was submitted to the database of NCBI.

1.7 Study on Enzyme Production Characteristics of SDF-25 Strain

The SDF-25 strains were inoculated into 50 mL of liquid enzyme production medium. The inoculation amount, and the initial pH and temperature of the medium (the other culture conditions remained unchanged) were sequentially optimized. The activity of the enzymes produced by the SDF-25 strains after 3 d was determined. The inoculation amount was 1%, 2%, 3% and 4%, respectively. The initial pH was 5, 6, 7, 8, 9 and 10, respectively. The temperature was 6° C., 10° C., 16° C., 28° C., and 37° C., respectively.

Figure 6:
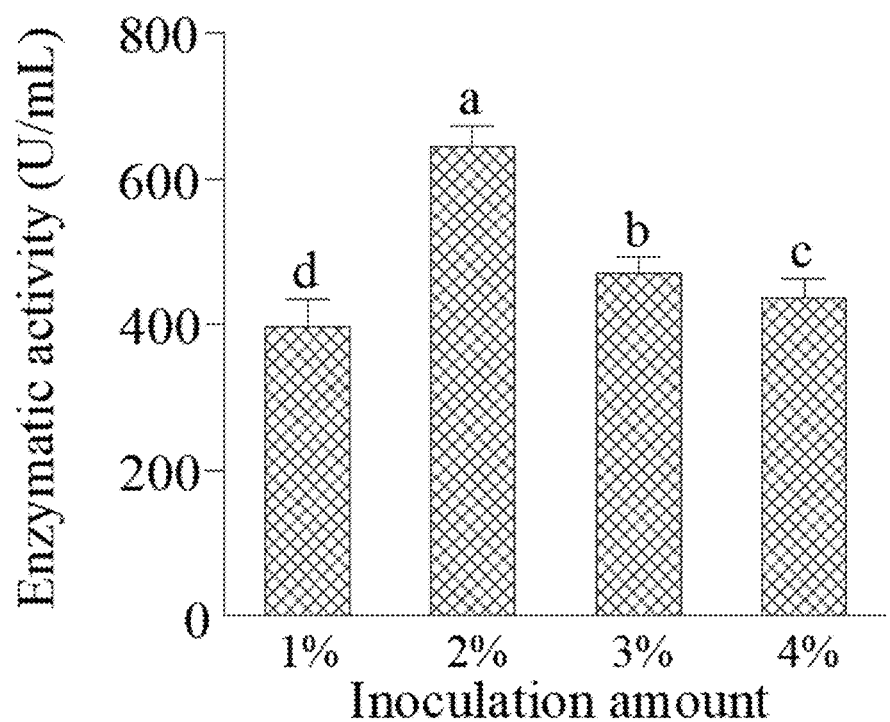
FIG. 6 is a column diagram of the activity of the enzymes produced by *Penicillium oxalicum* SDF-25 in different inoculation amounts in Embodiment 1 of the present application.

The SDF-25 strains were inoculated into the liquid enzyme production media according to different inoculation amounts, subjected to shaking culture at 16° C. for 72 h, and centrifuged. The supernatant was taken, and the enzymatic activity of a crude enzyme solution was determined. Results are shown in FIG. 6. The inoculation amount had a significant effect on the enzymatic activity. With an increase in the inoculation amount, the enzymatic activity increased first and then decreased. When the inoculation amount was 2%, the enzymatic activity was the highest, reaching 644.5 U/mL. Too low or too high inoculation amounts significantly affected the enzymatic activity.

Figure 7:
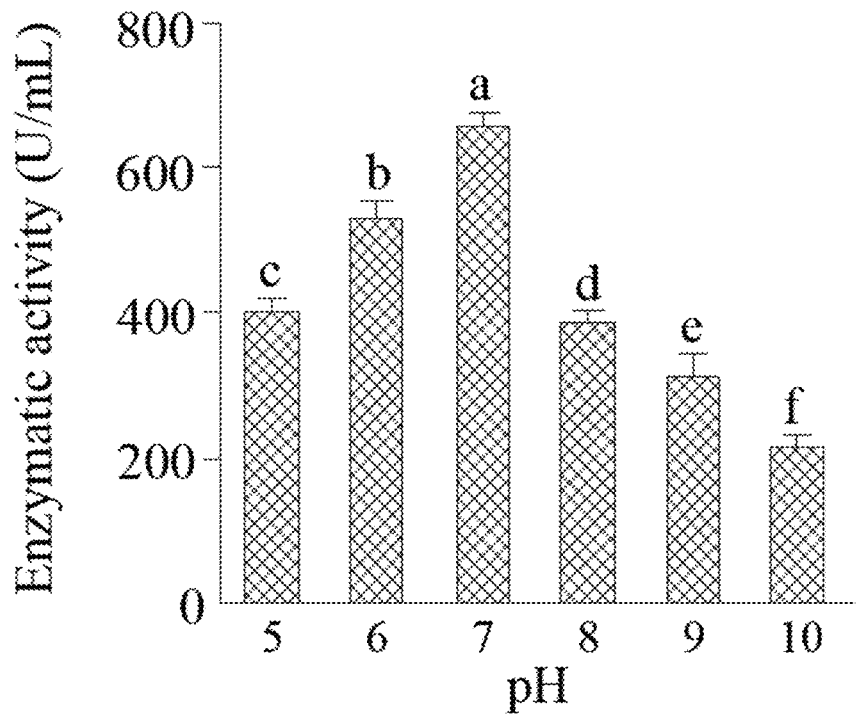
FIG. 7 is a column diagram of the activity of the enzymes produced by *Penicillium oxalicum* SDF-25 under different pH conditions in Embodiment 1 of the present application.

The enzyme production characteristics of the SDF-25 strain at different initial pH values are shown in FIG. 7. The enzymatic activities of carboxymethyl cellulase produced by the SDF-25 strain were also different at different initial pH values. The study results shown in FIG. 7 indicate that the initial pH value has a significant effect on the enzyme production ability of the strain: the activity of the enzymes produced by the SDF-25 strain increased first and then decreased with an increase in pH. When the initial pH was 7, the highest enzymatic activity was obtained, reaching 655.7 U/mL. In addition, the enzyme production activity of the SDF-25 strain under acidic conditions was higher than that under alkaline conditions.

Figure 8:
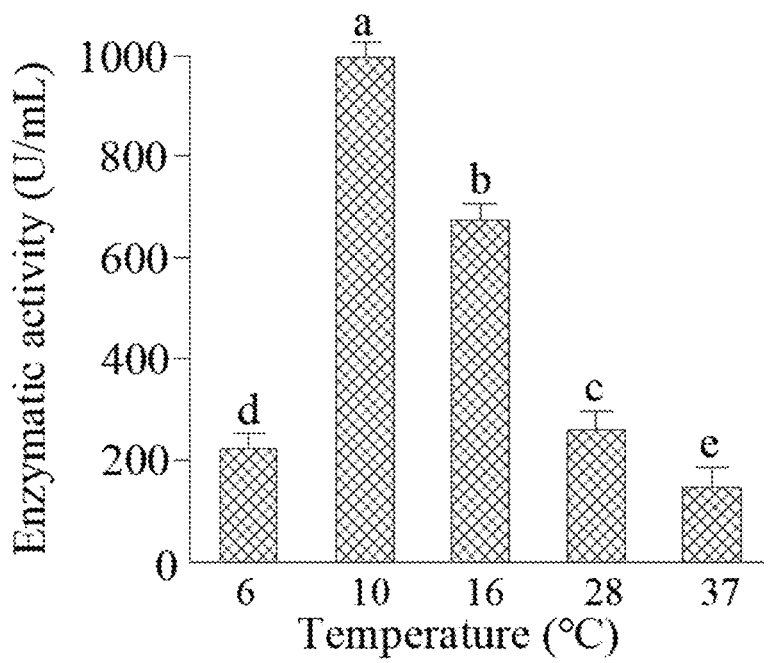
FIG. 8 is a column diagram of the activity of the enzymes produced by *Penicillium oxalicum* SDF-25 under different temperature conditions in Embodiment 1 of the present application.

The enzyme production characteristics of the SDF-25 strain at different temperatures are shown in FIG. 8. The activity of the enzymes produced by the SDF-25 strain increased first and then decreased with an increase in culture temperature. When the temperature was 10° C., the highest activity of enzymes produced by the SDF-25 strain was obtained, reaching 993.3 U/mL, followed by the activity at 16° C. The enzymatic activities of the SDF-25 strain decreased significantly at 28° C. and 37° C. Furthermore, it should be noted that the SDF-25 strain could still grow and produce enzymes at low temperature of 6° C., which indicated that the SDF-25 strain belongs to cold-tolerant bacteria.

1.8 Study on Degradation Rate of SDF-25 on Corn Straw

The SDF-25 strains were inoculated into a straw degradation medium. The inoculation amount, and the initial pH and temperature of the medium (other culture conditions remained unchanged) were sequentially optimized. The SDF-25 strains were subjected to static culture for 15 d, and the straw degradation rate of the strain was determined by the method shown in 1.5. The inoculation amount was 1%, 2%, 3% and 4%, respectively. The initial pH was 5, 6, 7, 8, 9 and 10, respectively. The temperature was 6° C., 10° C., 16° C., 28° C., and 37° C., respectively.

Figure 9:
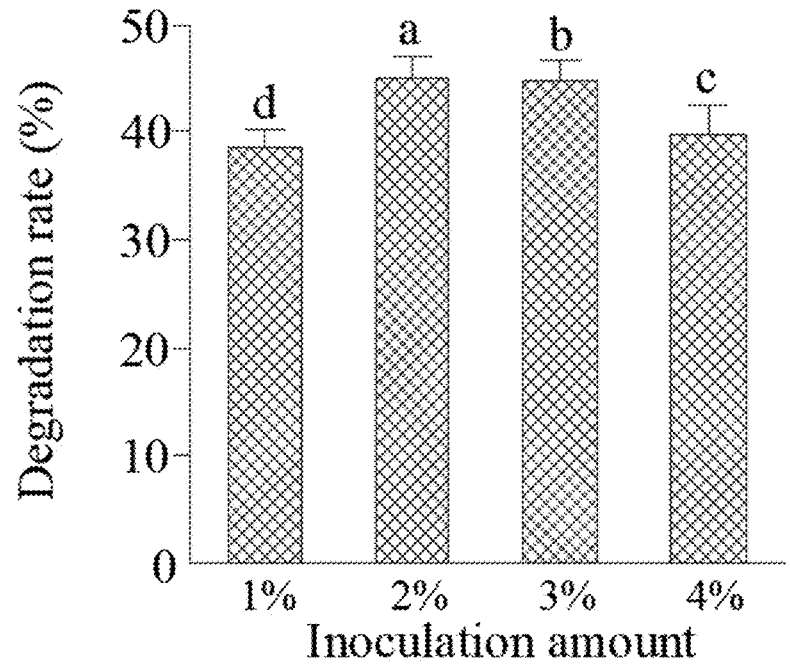
FIG. 9 is a column diagram of straw degradation rates of *Penicillium oxalicum* SDF-25 in different inoculation amounts in Embodiment 1 of the present application.

The SDF-25 strains were inoculated in the corn straw media according to different inoculation amounts, and subjected to static culture for 15 d. The results are shown in FIG. 9. With an increase in inoculation amount, the degradation rate increased first and then decreased. When the inoculation amount was 2%, the highest degradation rate was obtained, reaching 45-6%.

Figure 10:
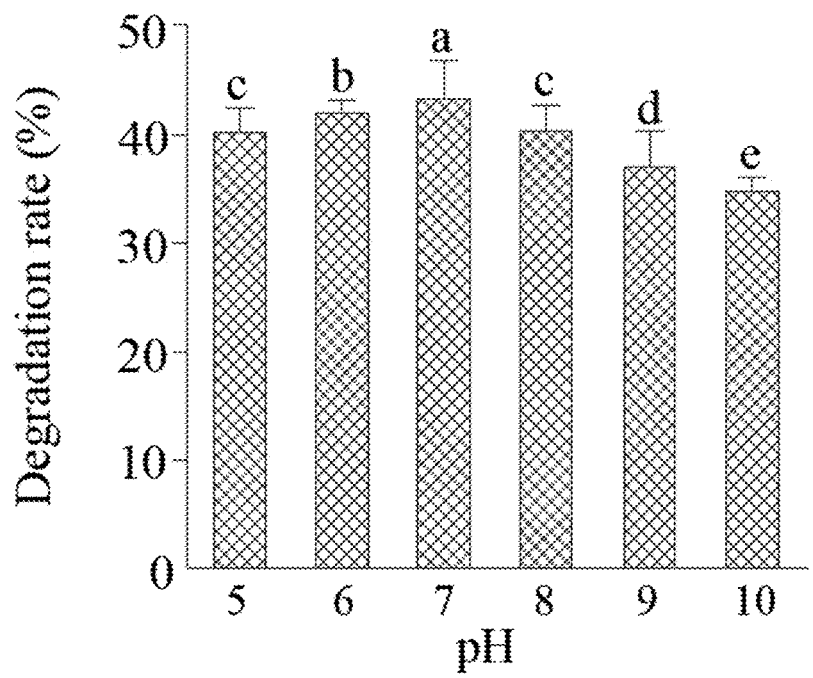
FIG. 10 is a column diagram of straw degradation rates of *Penicillium oxalicum* SDF-25 under different pH conditions in Embodiment 1 of the present application.

The degradation rates of the SDF-25 strain at different initial pH values are shown in FIG. 10. With an increase in pH, the degradation rate of SDF-25 strain on corn straw increased first and then decreased. The highest degradation rate was obtained at the initial pH value of 7, reaching 43.2%, followed by the degradation rate at the pH value of 6. In addition, it can also be seen from FIG. 10 that the SDF-25 strain had a higher degradation rate under acid conditions than that under alkaline conditions.

Figure 11:
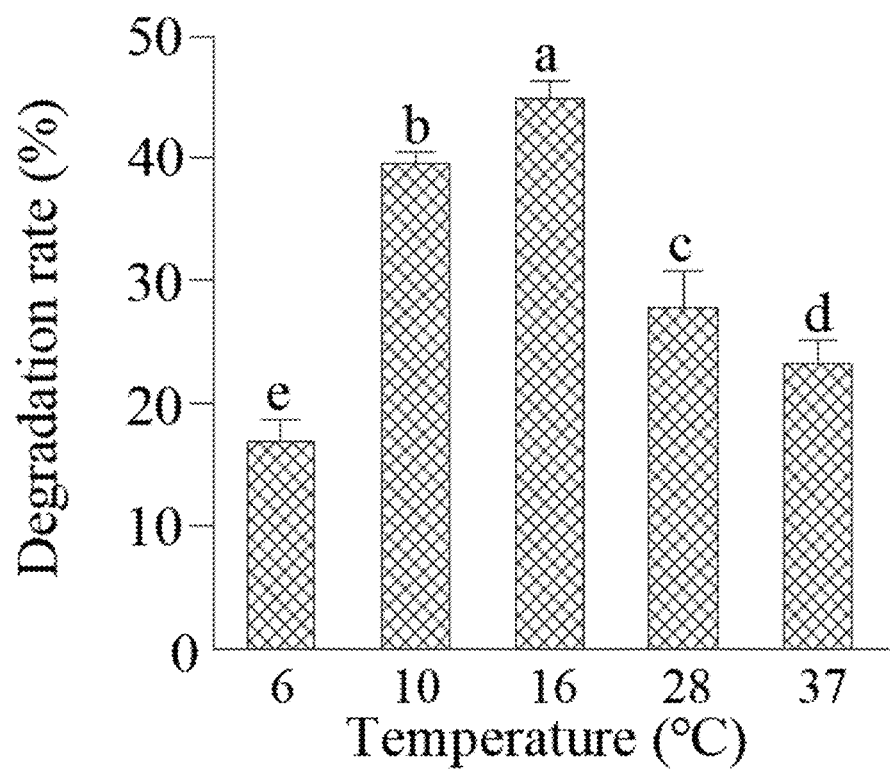
FIG. 11 is a column diagram of straw degradation rates of *Penicillium oxalicum* SDF-25 under different temperature conditions in Embodiment 1 of the present application.

The straw degradation rates of the SDF-25 strain under different culture temperatures are shown in FIG. 11. When the temperature was 16° C., the straw degradation rate of the SDF-25 strain reached 44.9%. The straw degradation rate of the SDF-25 strain could reach 39.5% at 10° C., which indicated that the SDF-25 strain still have strong straw degradation ability at low temperature.

The SDF-25 strain has been preserved in China General Microbiological Culture Collection Center and obtained the preservation number of CGMCC No. 19272, which belongs to *Penicillium oxalicum*.

Embodiment 2

*Penicillium oxalicum* SDF-25 (SDF-25 strains) screened in Embodiment 1 were used to prepare an inoculant which included an adsorption substrate and the *Penicillium oxalicum* SDF-25. *Penicillium oxalicum* SDF-25 could be in the form of bacterial powder and was combined with the adsorption substrate to form the inoculant. A preparation method of the inoculant specifically included the following process steps:

- step a: activation of *Penicillium oxalicum* SDF-25: *Penicillium oxalicum* SDF-25 stored at −80° C. was streaked onto a plate medium V (made of a PDA medium of Embodiment 1) and cultured at 16° C. for 24 h to obtain *Penicillium oxalicum* SDF-25 strains.
- step b: liquid culture: an inoculating loop was used to obtain hyphae from the activated *Penicillium oxalicum* SDF-25 strains obtained in step a. The hyphae were inoculated into a conical flask containing a PD medium (liquid), and subjected to shaking culture at 16° C. and 200 r/min for 48 h to obtain a *Penicillium oxalicum* SDF-25 strain culture broth.
- step c: fermentation: the *Penicillium oxalicum* SDF-25 strain culture broth obtained in step b was inoculated into a 10 L seeding tank, and fermented at 16° C. and 200 r/min for 2 d to obtain a *Penicillium oxalicum* SDF-25 strain fermentation broth, with the fermentation medium being a PD medium, and the inoculation volume of the *Penicillium oxalicum* SDF-25 strain culture broth being 5% of the volume of the PD medium (liquid).
- step d: amplification culture: the *Penicillium oxalicum* SDF-25 strain fermentation broth obtained by fermentation in step c was inoculated into a PD medium (liquid), and fermented at 16° C. and 200 r/min for 24 h to obtain a *Penicillium oxalicum* SDF-25 stain seed broth, with the inoculation volume of the *Penicillium oxalicum* SDF-25 strain seed broth being 3% of the volume of the PD medium (liquid).
- step e: the *Penicillium oxalicum* SDF-25 strain seed broth obtained in step d was centrifuged. The supernatant was removed, and a spore solution was collected. Light calcium carbonate was added into the collected spore solution and dried to obtain the *Penicillium oxalicum* SDF-25 strain inoculant.

Embodiment 3

The *Penicillium oxalicum* SDF-25 strain inoculant obtained in Embodiment 2 was used for field degradation of corn straw by the following specific degradation method. The *Penicillium oxalicum* SDF-25 strain inoculant was mixed with crushed straw in an inoculation amount of 0.5% by weight. The mixture was filled into bags with a length of 1 meter, a width of 0.8 meter, and an aperture of 0.12 mm, with each bag being filled with 700 g (dry weight) of crushed straw. Bags without the *Penicillium oxalicum* SDF-25 strain inoculant were used as a control group, and normal temperature strains were used as a positive control. The bags were buried in a wheat planting field in wheat planting season and taken out after 15 days. After objects in the bags were washed, a dry weight of the straw was obtained. A straw degradation rate was calculated, which reached 48.6%. The *Penicillium oxalicum* SDF-25 strain screened in the present application has a strong straw degradation ability and a high enzyme production activity under low temperature conditions, and is particularly suitable for straw degradation in cold regions and regions with a large temperature difference between day and night. In addition, the *Penicillium oxalicum* SDF-25 strain provided in the present application can reproduce and grow in a wide temperature range, and has strong adaptability.

---

The invention claimed is:

1. A method of degrading corn straw, the method comprising applying a *Penicillium oxalicum* SDF-25 to the corn straw, wherein the *Penicillium oxalicum* SDF-25 is preserved in China General Microbiological Culture Collection Center (CGMCC) with a preservation number of CGMCC NO.19272.

2. The method of claim 1, wherein the *Penicillium oxalicum* SDF-25 is in an inoculant.

3. The method of claim 2, wherein the inoculant further comprises an adsorption substrate.

4. The method of claim 3, wherein the adsorption substrate is light calcium carbonate.

5. The method of claim 2, wherein the *Penicillium oxalicum* SDF-25 has a concentration of no less than $2\times10^8$ colony forming units (cfu) in each gram of the inoculant.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
tcctccgctt attgatatgc                                               20

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
```

```
gaaggtgaag tcgtaacaag g                                              21

<210> SEQ ID NO 3
<211> LENGTH: 616
<212> TYPE: DNA
<213> ORGANISM: PENICILLIUM OXALICUM

<400> SEQUENCE: 3
ttcctccgct tattgatatg cttaagttca gcgggtatcc ctacctgatc cgaggtcaac      60
ctggttaaga ttgatggtgt tcgccggcgg gcgccggccg ggcctacaga gcgggtgacg     120
aagccccata cgctcgagga ccggacgcgg tgccgccgct gcctttcggg cccgccccc     180 ggaagcgggg ggcgagagcc caacacacaa gccgtgcttg agggcagcaa tgacgctcgg    240
acaggcatgc cccccggaat accaggggc gcaatgtgcg ttcaaagact cgatgattca     300
ctgaattctg caattcacat tacttatcgc atttcgctgc gttcttcatc gatgccggaa    360
ccaagagatc cgttgttgaa agttttaact gatttagtca agtactcaga ctgcaatctt    420
cagacaagag ttcgtttgtg tgtcttcggc gggcgcgggc ccggggggcgg atgccccccg   480 gcggccgtga ggcgggcccg ccgaagcaac aaggtacgat aaacacgggt gggaggttgg    540
acccagaggg ccctcactcg gtaatgatcc ttccgcaggt tcacctacgg aaaccttgtt    600
acgactttca ccatca                                                    616
```